United States Patent [19]

McMorrow, Jr.

[11] 4,200,109
[45] Apr. 29, 1980

[54] COUPLING CIRCUIT WITH DRIVEN GUARD

[75] Inventor: Richard H. McMorrow, Jr., Lincoln, Mass.

[73] Assignee: Hewlett-Packard Company, Palo Alto, Calif.

[21] Appl. No.: 940,405

[22] Filed: Sep. 7, 1978

[51] Int. Cl.² .............................................. A61B 5/04
[52] U.S. Cl. .................................... 128/696; 128/908
[58] Field of Search ................. 128/2.06 A, 696, 901, 128/902, 903, 639–643, 908, 709

[56] References Cited

U.S. PATENT DOCUMENTS

| | | | |
|---|---|---|---|
| 3,690,313 | 9/1972 | Weppner et al. | 128/902 |
| 3,757,778 | 9/1973 | Graham | 128/902 |
| 3,868,948 | 3/1975 | Graetz | 128/709 |
| 3,915,154 | 10/1975 | Cosentinc | 128/908 |
| 4,023,565 | 5/1977 | Ohlsson | 128/709 |

Primary Examiner—William E. Kamm
Attorney, Agent, or Firm—Donald N. Timbie

[57] ABSTRACT

In signal measurement circuits which are referred to a floating ground and which derive their input signals from electrodes attached to a patient's body, the effects of common mode potentials on the patient's body are minimized without requiring any patient electrodes other than those acting as signal sources, by using an operational amplifier to drive the floating ground toward the common mode potential on the patient's body.

This process is accomplished without significantly degrading the isolation impedance between the measurement circuits and true ground.

The patient is protected from hazardous electrical shock by incorporating a current limiting impedance in the amplifier circuit.

2 Claims, 1 Drawing Figure

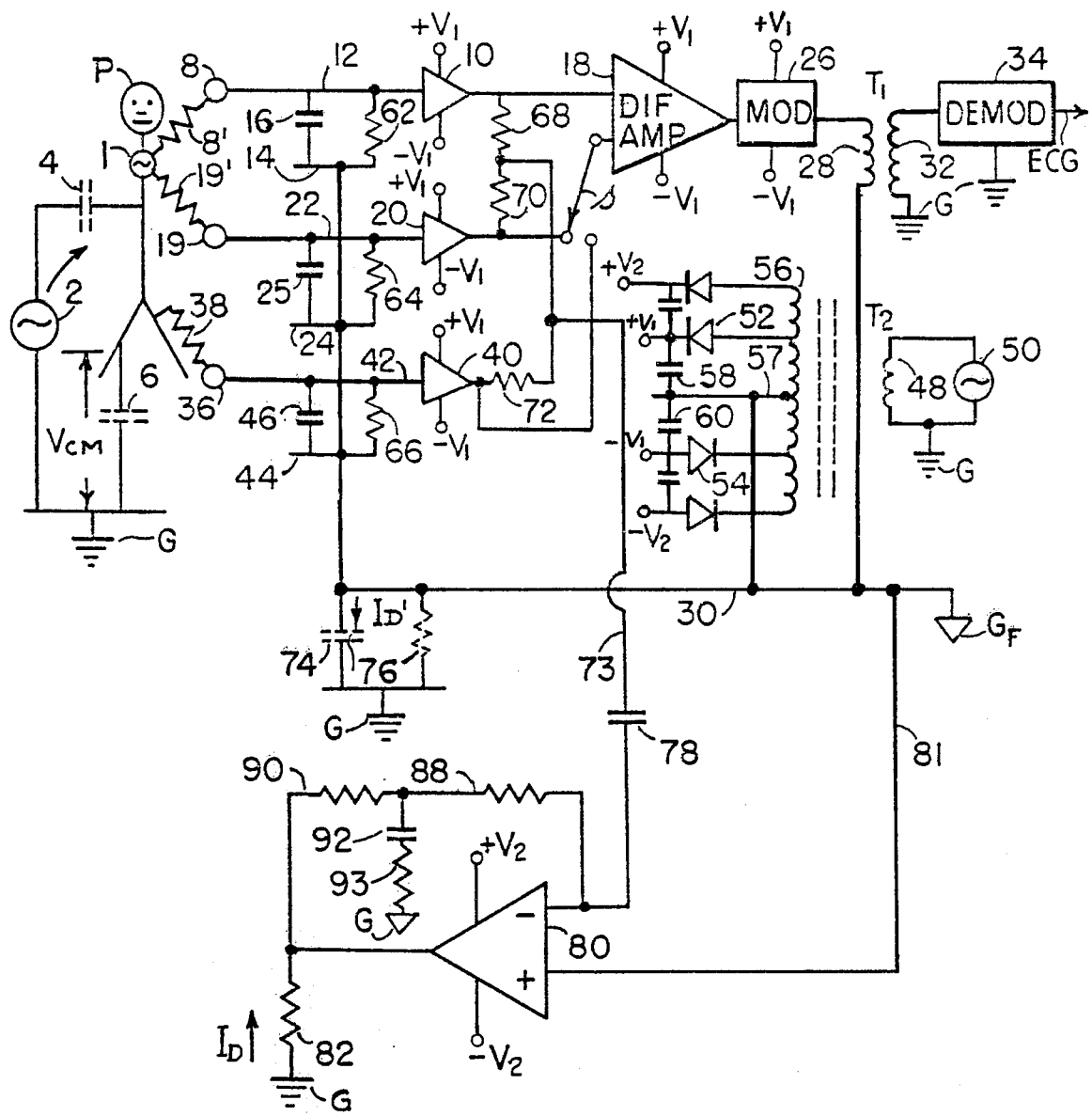

COUPLING CIRCUIT WITH DRIVEN GUARD

BACKGROUND OF THE INVENTION

In monitoring the condition of a patient's heart, potentials produced by heart action at different points on the body are picked up by electrodes applied to these points and the differences between the potentials are coupled via suitable circuits to the monitoring apparatus that is referenced to true ground. In order to protect the patient from the possibility of electrical shock, any path between the patient and true ground must have a very high impedance. Accordingly, any circuit that is directly coupled to the patient is referenced to a floating ground called a "guard". Unfortunately, however, the patient is generally within one or more ambient electrical fields from such sources as lights or power cords that produce what is known as a "common mode voltage", $V_{CM}$, on his body. The impedance looking back from each electrode to the patient's body and the impedance looking forward from each electrode to the floating ground form a conventional four-element bridge circuit which is excited by some fraction of the $V_{CM}$. If the bridge happens to be in balance, the $V_{CM}$ introduces no problem, but this is seldom if ever the case because the impedance between each electrode and the patient's body can vary over wide limits. Any imbalance causes a portion of the common mode potential $V_{CM}$ to add to or subtract from the difference between the potentials at the points of interest on the body so as to cause errors in the signal derived therefrom.

A solution to this problem that has been used for a long time is to apply a reference electrode to the patient's body and connect it to the floating ground or guard in such manner as to make the patient have nearly the same potential as the guard, thereby reducing the effect of the common mode voltage on the floating circuit.

Whereas this scheme works well, the reference electrode is a source of error if it is not properly applied, so that as much care and time must be taken in applying it to the patient's body as in applying the other electrodes. Furthermore, because it provides no useful physiological information it therefore may be a source of confusion to a user.

In his U.S. patent application filed concurrently herewith and entitled "Coupling Circuit With Driven Guard", Timothy B. Blancke has described an invention that eliminates the need for a reference electrode without in any way impairing the safety of the patient. At the same time, excellent rejection of the effects of common mode potentials is attained. The circuits connected to the patient are referred to floating ground or guard as before, but instead of driving the potential of the patient toward the common mode potential of the guard, as has been done, the guard is driven toward the common mode potential of the patient. This is accomplished by applying the common mode potential on the floating circuits to control means for causing current to flow from true ground through the stray impedance between guard and true ground. If the current has the correct value and direction, the guard will have the same common mode potential as the floating circuits. Under such conditions, the bridge is not excited by the common mode potential and no addition to or subtraction from the desired signal voltages occurs.

In order to protect the patient from electrical shock, the circuits shown in the application referred to utilize current limiters. Such devices are expensive and subject to failure. In his U.S. patent application entitled "Coupling Circuit with Driven Guard", filed concurrently herewith, Dr. Arthur Miller describes a circuit that functions in a similar manner to the circuit shown in Mr. Blancke's application in which the patient is protected from electrical shock without the use of current limiters. The present invention also obviates the use of current limiters to protect the patient from electrical shock, but instead of using a buffer amplifier as a current supply means to maintain the common mode potential of the guard the same as that of the patient, it utilizes an operational amplifier to perform the function.

Briefly, this may be accomplished in accordance with this invention by coupling the inverting input of an operational amplifier to a point on the floating circuits and connecting its non-inverting input to the floating ground. A large impedance for protecting the patient is connected between the output of the amplifier and true ground, and the power supply for the amplifier is referred to floating ground.

The drawing illustrates the general type of circuit used for deriving a signal proportional to the voltage difference between a pair of electrodes applied to the patient's body. Stray impedances are shown in dotted lines. Source 1 supplies the desired differential physiological signals, and the numeral 2 indicates a source of undesired ambient potentials such as may be introduced by a power cord. The source 2 is shown as being coupled to a patient P via a stray capacitance represented by a capacitor 4. The common mode potential, $V_{CM}$, is at all points on the patient's body and its amplitude relative to that of the ambient potential depends on the voltage dividing action of the stray capacitance represented by a capacitor 4 and the stray capacitance between the patient and true ground that is represented by the capacitor 6. The impedance between a right arm electrode 8 and the patient'body is represented by a resistor 8'. The electrode 8 is connected to an input of a unity gain buffer amplifier 10 via a lead 12, and the distributed capacitance between the lead 12 and its shield 14 is represented by a capacitor 16. The output of the amplifier 10 is connected to an input of a difference amplifier 18. Similarly, a left arm electrode 19 having an impedance between it and the patient's body represented by a resistor 19' is connected to an input of a unity gain buffer amplifier 20 via a lead 22. The distributed capacitance between the lead 22 and its shield 24 is represented by a capacitor 25. The output of the amplifier 20 is connected via one terminal of a switch s to the other input of the difference amplifier 18. Although the coupling of the buffer amplifiers to the difference amplifier 18 may include a Wilson network, this is not shown in order to simplify the drawing.

The output of the difference amplifier 18 is coupled to a modulator 26 that may be one of many types. A primary winding 28 of a transformer T₁ is connected between the output of the modulator 26 and a guard bus 30 that is connected to a floating ground or guard indicated at $G_F$. The secondary winding 32 of the transformer T₁ is connected between true ground, G, and a demodulator 34 which derives the ECG signal at its output.

If other electrodes are used, as in a selectable lead or multivector system, they would be coupled to the difference amplifier 18 in a manner similar to the way in which the electrodes 8 and 19 are coupled, e.g., an electrode 36 having an impedance between it and the patient's body represented by a resistor 38 is connected to the input of a buffer amplifier 40 via a lead 42. The distributed capacitance between the lead 42 and its shield 44 is represented by a capacitor 46. The output of the amplifier 40 is connected to another terminal of the switch s. In the position shown, the switch s conducts the signal at the output of the buffer amplifier 20 to the difference amplifier 18, but with the switch s in its other position, it conducts the signal at the output of the buffer amplifier 40 to the difference amplifier 18.

The circuits directly coupled to the patient are referenced to a floating ground or guard by supplying them with operating potentials, $+V_1$ and $-V_1$, that are positive and negative with respect to the guard $G_F$. These potentials are applied to the buffer amplifiers 10, 20 and 40, the difference amplifier 18, and the modulator 26. The power supply is comprised of a transformer $T_2$ having a primary winding 48 connected at one end to true ground G and in shunt with a source of alternating current voltage 50. Oppositely poled diodes 52 and 54 are respectively connected between the ends of a secondary winding 56 of the transformer $T_2$ and its center tap 57 via capacitors 58 and 60. The guard bus 30 is connected to the center tap 57 and to the shields 14, 24 and 44. It will be understood by those skilled in the art that whereas separate transformers $T_1$ and $T_2$ are respectively used for coupling signals and providing power, techniques exist for performing both of these functions with a single transformer; but however this is accomplished, the circuits directly connected to the patient P and the primary winding 28 of the transformer $T_1$ are to be referenced to floating ground or guard $G_F$.

THE PROBLEM

The patient's body and the floating ground $G_F$, which is the point to which the inputs of the buffer amplifiers 10 and 20 are referred, are a first set of diagonally opposed points of a bridge circuit, and the electrodes 8 and 19 are a second set. One pair of arms of the bridge are formed by the impedances 8' and 19' between the patient's body and the electrodes 8 and 19, and the other pair of arms are formed by capacitances 16 and 25. The input impedances of the amplifiers 10 and 20 are so large as to have little effect on the bridge circuit even though they are part of it. Whereas the impedances of the capacitors 16 and 25 can be made very nearly equal, the impedances 8' and 19' are very seldom equal because they depend on the variable factors involved in the application of the electrodes 8 and 19 to the body. Inasmuch as the source 1 of ECG potentials is connected in series with the arms of the bridge, imbalance in the bridge per se has no effect on the form of the ECG voltages delivered to the buffer amplifiers 10 and 20, but because a substantial fraction of the commom mode potential $V_{CM}$ is connected between the first set of diagonal points of the bridge, namely, the patient's body and the floating ground $G_F$, any imbalance will cause unequal fractions of the commom mode potential to appear at the electrodes 8 and 19 which are the second set of diagonal points of the bridge. This converts the commom mode interference voltage to a differential signal applied to the buffer amplifiers 10 and 20. Because the commom mode potential $V_{CM}$ is much larger than the ECG potentials, even a small imbalance in the bridge can cause a differential interference signal at the input of the difference amplifier 18 that is larger than the desired ECG voltages.

THE SOLUTION

The circuit described below drives the floating ground $G_F$ toward the potential $V_{CM}$ so that the fraction of the common mode voltage which excites the bridge circuit is greatly reduced. Therefore, regardless of the degree of imbalance in the bridge, smaller interference signals appear at the electrodes 8 and 19. If the voltage on $G_F$ is made equal to $V_{CM}$, the bridge excitation and the resulting interference becomes zero.

The following components of the circuit are common to the invention of the application referred to and to the invention of this application. Bias current resistors 62, 64 and 66 are respectively connected between the inputs of the buffer amplifiers 10, 20 and 40 and the bus 30. Resistors 68, 70 and 72 of equal value are respectively connected between the outputs of the buffer amplifiers 10, 20 and 38 and a lead 73. Since the output impedance of the buffer amplifiers is low, these resistors have negligible loading effect, and they do not affect the form or magnitude of the ECG signal. A dotted capacitor 74 and a dotted resistor 76 that are shown in parallel between the bus 30 and true ground represent the distributed impedance between the guard $G_F$ and true ground.

EMBODIMENT OF THIS INVENTION

The common mode voltage $V_{CM}$ on the lead 73 is coupled via a capacitor 78 to the inverting input of an operational amplifier 80, and the floating ground bus 30 is connected to the non-inverting input of the amplifier 80 via a lead 81. The output of the amplifier 80 is coupled to ground by an impedance, herein indicated as being resistor 82, of sufficient magnitude to protect the patient from electrical shock should he come in direct contact with some otherwise harmful voltage. A capacitor or capacitor and resistor in parallel could also be used. Operating potentials $+V_2$ and $-V_2$ that are referred to floating ground are provided by coupling suitable rectifying means 84 and 86 to opposite ends of the secondary winding 56 of the transformer $T_2$. In order to prevent DC latchup, resistors 88 and 90 are connected in series between the inverting input of the amplifier 80 and its output. A capacitor 92 is connected between the junction of the resistors 88 and 90 and floating ground via a resistor 93.

The operation of the circuit may be understood by noting that the inverting input of the operational amplifier 80 is coupled to the junction of the resistors 68 and 70 via the lead 73 so that the output of the amplifier 80 always has a polarity opposite to the relative polarity between the common mode potential on the circuit and the common mode potential on the bus 30 of floating ground. Thus, if the common mode voltage $V_{CM}$ at the junction of the resistors 68 and 70 is positive with respect to the $V_{CM}$ on the bus 30, the output of the amplifier 80 is negative and the current in the resistor 82 is in the direction indicated by the arrow $I_D$. This will cause a current to flow through the stray impedances 74 and 76 in a direction indicated by the arrow $I_D$, so as to make the bus 30 positive. Looking at it another way, the operational amplifier 80 maintains the voltages at its inputs equal so that the voltage at the junction of the resistors 68 and 70 is always the same as the voltage of the floating ground bus 30.

It can be seen that the operational amplifier 80 supplies current between true ground and the guard bus 30 and that the current is controlled by the commom mode potential $V_{CM}$ (Note that the amplifier 80 obtains current from true ground via the power supply of $+V_2$ and $-V_2$.) coupled to the inverting input, so as to make the guard bus 30 have the same common mode potential as that on the patient's body and at the junction of the resistors 68 and 70.

It will be apparent that the resistors 68, 70 and 72 that couple the common mode potential on the floating circuits to the lead 73 could be connected to the inputs of the buffer amplifiers 10, 20 and 38 respectively and that, in either case, only one of the resistors needs to be used. It would also be possible to use only one buffer amplifier, in which case the direct connection replacing the other buffer amplifier would be guard.

I claim:

1. In combination,
   a circuit referred to a floating ground for coupling electrodes to equipment that is referred to true ground,
   an operational amplifier having an inverting input, a non-inverting input and an output,
   a capacitor coupled between a point on said circuit and said inverting input,
   means coupling said non-inverting input to a point of floating ground potential,
   an impedance connected between said output of said amplifier and true ground, and
   means for supplying operating potentials to said operational amplifier that are referred to floating ground.

2. A circuit as set forth in claim 1 wherein first and second resistors are connected in series between said output of said amplifier and its inverting input, and wherein a capacitor is connected between the junction of said first and second resistors and a point of floating ground potential.

* * * * *